(12) United States Patent
Mazereeuw et al.

(10) Patent No.: US 8,766,041 B2
(45) Date of Patent: Jul. 1, 2014

(54) MARKER GENETICALLY LINKED TO TOBAMOVIRUS RESISTANCE IN CUCUMBER AND THE USE THEREOF

(75) Inventors: Jaap Mazereeuw, Enkhuizen (NL); Brigit Van Kampen, Horst (NL); Nanne Faber, Hoorn (NL); Ronald Wilterdink, Enkhuizen (NL)

(73) Assignee: Enza Zaden Beheer B.V., Enkhuizen (NL)

(*) Notice: Subject to any disclaimer, the term of this patent is extended or adjusted under 35 U.S.C. 154(b) by 381 days.

(21) Appl. No.: 12/811,790

(22) PCT Filed: Jan. 10, 2008

(86) PCT No.: PCT/EP2008/000145
§ 371 (c)(1),
(2), (4) Date: Aug. 5, 2010

(87) PCT Pub. No.: WO2009/086850
PCT Pub. Date: Jul. 16, 2009

(65) Prior Publication Data
US 2010/0299786 A1    Nov. 25, 2010

(51) Int. Cl.
*A01H 1/04* (2006.01)
*A01H 1/02* (2006.01)
*A01H 5/08* (2006.01)

(52) U.S. Cl.
USPC ............ 800/307; 800/265; 800/266; 800/267

(58) Field of Classification Search
None
See application file for complete search history.

(56) References Cited

FOREIGN PATENT DOCUMENTS

| EP | 1188833 A | 3/2002 |
|----|-----------|--------|
| WO | 0109300 A | 2/2001 |
| WO | 02063019 A | 8/2002 |

OTHER PUBLICATIONS

Gibbs, Phil. Trans. R. Soc. Lond. B, (1999), pp. 593-602.*
International Preliminary Report on Patentability in related International Patent Application No. PCT/EP2008/000145, dated Jul. 13, 2010.
International Search Report dated Oct. 1, 2008 (PCT/EP2008/000145); ISA/EP.
Database CABA [Online] Grin'ko, N. N. : "Mosaic disease of greenhouse cucumbers" XP002496438 retrieved from STN Database accession No. 2005:109528, abstract & Zashchita I Karantin Rastenii , No. 11, pp. 21-22. Publisher: Izdatel 'Stvo Kolos. Moscow ISSN: 1026-8634, 2004.
Database CABA [Online] Trusevich, A. V. et al: "Cucumber diseases in greenhouses" XP002496439 retrieved from STN Database accession No. 2003:53076, abstrac & Zashchita I Karantin Rastenii, No. 10, pp. 20-23. Publisher: Izdatel 'Stvo Kolos. Moscow ISSN: 0044-1864, 2002.
Amit Gal-On et al: "Transgenic cucumbers harboring the 54-kDa putative gene of Cucumber fruit mottle mosaic tobamovirus are highly resistant to viral infection and protect non-transgenic scions from soil infection" Transgenic Research, Kluwer Academic Publishers-Plenum Publishers, NE, vol. 14, No. 1, Feb. 1, 2005, pp. 81-93, XP019269415; ISSN: 1573-9368; abstract.
Sitterly WR: "Breeding for disease resistance in cucurbits" Annu. Rev. Phytopathol., vol. 10, 1972, pp. 471-490, XP002496437 the whole document.

* cited by examiner

*Primary Examiner* — Brent T Page
*Assistant Examiner* — Jared Shapiro
(74) *Attorney, Agent, or Firm* — The Webb Law Firm

(57) ABSTRACT

The present invention relates to a molecular marker genetically linked to, and capable of identifying, a genetic locus in the cucumber plant (*Cucumis sativus* L.) genome conferring a general resistance against tobamoviruses, and especially against two commercially important pathogenic tobamoviruses, i.e., cucumber green mottle mosaic virus (CGMMV) and cucumber fruit mottle mosaic virus (CFMMV). The present invention further relates to methods for providing a cucumber plant (*Cucumis sativus* L.), plants, plant parts and fruits with resistance against tobamoviruses, and especially against two commercially important pathogenic tobamoviruses, i.e., cucumber green mottle mosaic virus (CGMMV) and cucumber fruit mottle mosaic virus (CFMMV).

5 Claims, No Drawings

```
SEQUENCE LISTING

<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: primer

<400> SEQUENCE: 1
gactgcgtac caattcgt                                                  18

<210> SEQ ID NO 2
<211> LENGTH: 18
<212> TYPE: DNA
<213> ORGANISM: Artificial Sequence
<220> FEATURE:
<223> OTHER INFORMATION: primer

<400> SEQUENCE: 2
gatgagtcct gagtaaca                                                  18

<210> SEQ ID NO 3
<211> LENGTH: 18
<212> TYPE: DNA
<213> ORGANISM: Artificial Sequence
<220> FEATURE:
<223> OTHER INFORMATION: primer

<400> SEQUENCE: 3
gactgcgtac caattcat                                                  18

<210> SEQ ID NO 4
<211> LENGTH: 18
<212> TYPE: DNA
<213> ORGANISM: Artificial Sequence
<220> FEATURE:
<223> OTHER INFORMATION: primer

<400> SEQUENCE: 4
gatgagtcct gagtaacg                                                  18
```

MARKER GENETICALLY LINKED TO TOBAMOVIRUS RESISTANCE IN CUCUMBER AND THE USE THEREOF

The present application is a national phase filing of international application No. PCT/EP2008/000145, filed Jan. 10, 2008, to which the present application claims priority and benefit of, and which is incorporated by reference herein in its entirety.

The Sequence Listing associated with this application is filed in electronic format via EFS-Web and is hereby incorporated by reference into the specification in its entirety. The name of the text file containing the Sequence Listing is 123306_ST25.txt. The size of the text file is 1,114 bytes, and the text file was created on Feb. 7, 2014.—

The present invention relates to a molecular marker genetically linked to, and capable of identifying, a genetic locus in the cucumber plant (*Cucumis sativus* L.) genome conferring a general resistance against tobamoviruses, and especially against two commercially important pathogenic tobamoviruses, i.e., cucumber green mottle mosaic virus (CGMMV) and cucumber fruit mottle mosaic virus (CFMMV).

The present invention further relates to methods for providing a cucumber plant (*Cucumis sativus* L.), plants, plant parts and fruits with resistance against tobamoviruses, and especially against two commercially important pathogenic tobamoviruses, i.e., cucumber green mottle mosaic virus (CGMMV) and cucumber fruit mottle mosaic virus (CFMMV).

Cucumber plants (i.e. plants of the botanical species *Cucumis sativus*) belong to the gourd family of Cucurbitaceae, also comprising family members like melons and squash.

The edible fruits of the plant are generally designated as cucumbers. Cucumbers usually are cylindrical, green skinned fruits, comprising approximately 96% water. The cucumber plant *Cucumis sativus* L., which has been cultivated since long, is an important horticultural crop worldwide. Cucumbers are commonly harvested in an unripe stadium and may be used for the pickle industry or the fresh market.

The cucurbit-infecting tobamoviruses can be separated into two subgroups: subgroup I comprising the strains and isolates referred to in literature as cucumber green mottle mosaic virus (CGMMV, comprising the strains CV3, CV4, CGMMV-W, CGMMV-SH and CGMMV-Is), and subgroup II comprising cucumber fruit mottle mosaic virus (CFMMV), Kyuri green mottle mosaic virus (KGMMV), and the Yodo strain of CGMMV, which is closely related to KGMMV and may be considered a strain of it (Antigus, 2001).

Cucumber green mottle mosaic virus (CGMMV) is a RNA virus of the genus tobamovirus causing a severe disease of Cucurbits.

Strains of CGMMV were first reported from the United Kingdom and Europe (Ainsworth, 1935). The virus is present in all tissues (Hollings, 1975) and the virus is rapidly transmitted on workers hands, clothing, knives and other equipment and is also seed-borne. Heat treatment of seeds is commonly used to control viral contamination of seeds (Kim, 2003). CGMMV can also spread via surface water (Drost, 1988).

Symptoms of yellowing, mottling and down-curling of the leaves have been reported though perhaps most significant are reports of moderate-severe fruit mottling and distortion. Such mottling and distortion of the fruit could quickly render infected crops unmarketable.

Cucumber green mottle mosaic virus (CGMMV) is perhaps the most widespread and renowned of the tobamoviruses infecting cucumber crops. CGMMV is a worldwide problem in cucumber production areas like The Netherlands, Spain (Celix, 1996), Greece (Varveri, 2002) and India (Rashmi, 2005). Yield losses may be 15% (Fletcher, 1962). Attempts of finding resistance in cucumber against CGMMV have been made (Hsiao, 1993) and some symptomless varieties from Asiatic origin have been found (Kooistra, 1968).

CFMMV is another family member of the tobamoviruses causing significant economic damage to cucumber plants (*Cucumis sativus* L.). Symptoms of cucumber fruit mottle mosaic virus (CFMMV) infection are generally first recognized on fruits and apical leaves at a relatively advanced growth stage. Leaf symptoms include severe mosaic, vein banding and yellow mottling. In some cases, fully developed plants show severe wilting symptoms that lead to plant collapse. Rapid viral spread within greenhouses may lead to significant crop losses.

Considering the economic damages caused by tobamoviruses in cucumber plants (*Cucumis sativus* L.), and especially CGMMV and CFMMV, including their variants, providing genetic markers genetically linked to, and capable of identifying, genetic resistance loci against tobamoviruses, or Qualitative Trait Loci (QTLs), and transferring this tobamoviruses resistance into economically important *Cucumis sativus* L. varieties is highly desirable.

Therefore, it is an object of the present invention to provide such genetic marker.

According to a first aspect, the present invention provides a method for providing a tobamovirus resistant cucumber plant (*Cucumis sativus* L.) comprising:

(a) identifying a tobamovirus resistance genetic locus in a first cucumber plant (*Cucumis sativus* L.);

(b) transferring the identified tobamovirus resistance genetic locus into a second cucumber plant (*Cucumis sativus* L.) thereby conferring tobamovirus resistance to said second cucumber plant (*Cucumis sativus* L.);

wherein the tobamovirus resistance genetic locus is characterized by the presence of a nucleic acid amplification fragment of 241 to 251 bp using molecular amplified fragment length polymorphism (AFLP) primers SEQ ID No: 1 and SEQ ID No: 2 in a molecular amplified fragment length polymorphism (AFLP) assay.

According to the present invention, primer SEQ ID No: 1 comprises the nucleic acid sequence 5-GAC TGC GTA CCA ATT CGT-3' and primer SEQ ID No: 2 comprises the nucleic acid sequence 5'-GAT GAG TCC TGA GTA ACA C-3'.

The molecular amplified fragment length polymorphism (AFLP) marker genetically linked to, and capable of identifying, the present tobamovirus resistance genetic locus is also designated herein as Marker E22/M48-F-246 (size nucleic acid AFLP amplification fragment: 241-251 bp, preferably 245-247 bp, most preferably 246 bp, when using primers SEQ ID Nos: 1 and 2).

The first cucumber plant (*Cucumis sativus* L.) according to the present invention can be any cucumber plant (*Cucumis sativus* L.) having a resistant phenotype for tobamoviruses, and especially CGMMV and CGMMV, conferred by the genetic locus identifiable by the presence of the nucleic acid amplification fragment as defined above (Marker E22/M48-F-246).

The presence of the nucleic acid amplification fragment, or molecular AFLP Marker E22/M48-F-246, and thereby the present resistance conferring genetic locus, can be established using any suitable Molecular Biology technique for analyzing nucleic acid amplification products such as gel electroforeses, hybridization, affinity chromatography, fluorescence, etc.

In a particularly preferred embodiment, the fragments are amplified and identified using a nucleic acid amplification and detection technique designated in the art as molecular amplified fragment length polymorphism (AFLP, Zabeau, 1993, and Vos, 1995).

Amplified fragment length polymorphism (AFLP) is a polymerase chain reaction (PCR) based genetic fingerprinting technique that was developed in the early 1990's by Keygene. AFLP uses restriction enzymes to cut genomic DNA, followed by ligation of complementary double stranded adaptors to the ends of the restriction fragments. A subset of the restriction fragments are then amplified using primer pairs complementary to the adaptor and restriction site fragments. The fragments are visualized on denaturing polyacrylamide gels either through autoradiographic or fluorescence methodologies.

This generally results in a multitude of nucleic acid amplification fragments of different sizes. By comparing the nucleic acid amplification fragments obtained from, for example, susceptible and resistant plants, discriminating nucleic acid amplification fragments can be identified, also designated as markers, between both phenotypes.

In the present case, a specific AFLP marker, designated as AFLP Marker E22/M48-F-246, genetically linked to, and capable of identifying, the present resistance locus was identified by the presence of a nucleic acid amplification fragment of 241-251 bp, preferably 245-247 bp, most preferably 246 bp. This marker was only present, amongst a number of non-discriminative other AFLP amplification fragments, in the resistant individuals and absent in the susceptible individuals.

It should be noted that AFLP analysis of cucumber plants (*Cucumis sativus* L.) using AFLP primers SEQ ID Nos: 1 and 2, in order to identify a tobamovirus resistance genetic locus in a first cucumber plant (*Cucumis sativus* L.), can yield a second nucleic acid amplification fragment having a size difference with the present AFLP Marker E22/M48-F-246 of 2 bp. According to the present invention, this larger (2 bp) nucleic acid amplification fragment is not genetically linked to, and capable of identifying, the present tobamovirus resistance genetic locus.

In other words, the present first cucumber plant (*Cucumis sativus* L.), when analyzed using AFLP and AFLP primers SEQ ID Nos: 1 and 2, must yield the present AFLP E22/M48-F-246 marker of the indicated size, but can, additionally, also yield a second nucleic acid amplification fragment of larger size (2 bp).

Both first cucumber plants (*Cucumis sativus* L.), i.e., yielding only AFLP Marker E22/M48-F-246, or yielding AFLP Marker E22/M48-F-246 and, additionally, a second slightly larger (2 bp) fragment, are encompassed by the present invention. However, first cucumber plants (*Cucumis sativus* L.) only yielding the second slightly larger (2 bp) fragment are not encompassed by the present invention.

Considering the above, the present selection of a first cucumber plant (*Cucumis sativus* L.) inherently comprises the detection of the tobamovirus resistance genetic locus in this plant using Molecular Biology techniques. This because the present tobamovirus resistance locus, genetically linked to AFLP Marker E22/M48-F-246, cannot be established using only phenotype based selection common to conventional breeding techniques.

In other words, identifying a tobamovirus resistance genetic locus in a first cucumber plant (*Cucumis sativus* L.) does not relate to using a sole conventional selection process.

After identification of the tobamovirus resistance genetic locus according to the present invention in a first cucumber plant (*Cucumis sativus* L.), the genetic locus is transferred into a second cucumber plant (*Cucumis sativus* L.) thereby conferring tobamovirus resistance to said second cucumber plant (*Cucumis sativus* L.)

Preferably, transferring the present tobamovirus resistance genetic locus comprises conventional breeding methods such as conventional crossing the first cucumber plant (*Cucumis sativus* L.) with the second cucumber plant (*Cucumis sativus* L.) and the subsequent one or more backcrossing with the second cucumber plant (*Cucumis sativus* L.). However, such conventional breeding methods are preferably assisted with molecular biology techniques to establish the maintenance of the present resistance genetic locus in the second cucumber plant (*Cucumis sativus* L.).

Compared to conventional breeding techniques, the provision of the present AFLP Marker E22/M48-F-246 according to the present invention allows for a rapid selection of suitable tobamovirus resistant offspring after every backcross step thereby avoiding laborious and expensive screening methods, such as viral infection and establishing a resistant phenotype, on every generation to identify suitable tobamovirus resistant offspring.

In a preferred embodiment, the second cucumber plant (*Cucumis sativus* L.) is a tobamovirus susceptible commercial variety. By transferring the present resistance genetic locus into this plant, while maintaining other commercially valuable high quality genotypic and phenotypic characteristics, a cucumber plant (*Cucumis sativus* L.) with increased economic value is provided.

In a most preferred embodiment, the present method provides a cucumber plant (*Cucumis sativus* L.) having the genotype of the second cucumber plant (*Cucumis sativus* L.) supplemented with a tobamovirus resistance genetic locus of the first cucumber plant (*Cucumis sativus* L.).

Therefore, the present invention also relates, according to a second aspect, to a cucumber plant (*Cucumis sativus* L.) comprising the genotype of a tobamovirus susceptible cucumber plant (*Cucumis sativus* L.) variety supplemented with a tobamovirus resistance genetic locus, wherein the tobamovirus resistance genetic locus is characterized by the presence of a nucleic acid amplification fragment of 241 to 251 bp, preferably 245 to 247 bp, most preferably 246 bp, using molecular amplified fragment length polymorphism (AFLP) primers SEQ ID No: 1 and SEQ ID No: 2 in a molecular amplified fragment length polymorphism (AFLP) assay.

The tobamovirus resistance, thus the tobamovirus resistance genetic locus according to the present invention, at least confers, in a preferred embodiment, resistance against cucumber green mottle mosaic virus (CGMMV) and cucumber fruit mottle mosaic virus (CFMMV).

According to a third aspect, the present invention relates to the use of a tobamovirus resistance genetic locus for providing tobamovirus resistant cucumber plant (*Cucumis sativus* L.) plant, wherein the tobamovirus resistance genetic locus is characterized as defined above.

According to this third aspect of the present invention, the tobamovirus resistance comprises cucumber green mottle mosaic virus (CGMMV) and cucumber fruit mottle mosaic virus (CFMMV) resistance.

According to a fourth aspect, the present invention relates to a tobamovirus resistance genetic locus characterized by a nucleic acid amplification fragment of 241 to 251 bp using molecular amplified fragment length polymorphism (AFLP) primers SEQ ID No: 1 and SEQ ID No: 2 in a molecular amplified fragment length polymorphism (AFLP) assay.

Preferably, the present tobamovirus resistance genetic locus is characterized by an AFLP nucleic acid amplification fragment of 245 to 247 bp.

Most preferably, the present tobamovirus resistance genetic locus is characterized by an AFLP nucleic acid amplification of 246 bp.

It should be noted that genetic loci, only indicated by an AFLP nucleic acid amplification fragment, using amplified fragment length polymorphism (AFLP) primers SEQ ID No: 1 and SEQ ID No: 2, being slightly larger (2 bp) in comparison with the above fragment, are not encompassed by the present invention.

According this fourth aspect of the present invention, the tobamovirus resistance preferably comprises cucumber green mottle mosaic virus (CGMMV) and cucumber fruit mottle mosaic virus (CFMMV) resistance.

The present invention will be further detailed in the accompanying examples.

EXAMPLES

Example I

Identification of Susceptible and Resistant Cucumber Plants (*Cucumis sativus* L.)

Introduction

The following protocol was used to classify cucumber plants (*Cucumis sativus* L.) as susceptible or resistant against a cucumber green mottle mosaic virus (CGMMV) and cucumber fruit mottle mosaic virus (CFMMV) infection. At least for the Netherlands, the best time to perform the analysis is from September until April.
Plant Material Plants (*Cucumis sativus* L.) to be tested, both resistant and susceptible, were sown in medium size vermiculite and grow at 24° C., covered with small size vermiculite. After 4 to 5 days (cotyledons just spread), the seedlings were transferred on Rockwool blocks and, after 2 days, the plants were transferred to a quarantine greenhouse.

After every block of 40 numbers, the susceptible control Tyria F1(commercial F1 cucumber variety of Enza Zaden, The Netherlands) is placed as a susceptible control, and the seedlings were inoculated on the cotyledons, preferably four days after placing them into the quarantine greenhouse.
Pathogen Isolates of CGMMV and CFMMV were prepared. Briefly, to prepare the inoculi, fresh phosphate buffer(0.1 M phosphate solution, pH of 7.7) was prepared. Leaf material from an infected cucumber plant (*Cucumis sativus* L.) of which the symptoms recently developed was picked. Young leaf tissue was taken without stems with clear symptoms. Approximately 1 gram of leaf material was used for 5 ml of buffer. The leaf material was grinded, thereby obtaining viral isolates.

For infection, when sunny weather appeared, the plants, as grown above, were shadowed with a cover one day before infection. One day after infection, the cover can be removed. However, in case of high light intensity, the cover should stay another day. In case of low humidity, the humidity can be increased by wetting the grey trays directly after infection to prevent shrivel up of the cotyledons due to damage of infection. Temperature regimes were 18-20° C. at night and 22-25° C. in the daytime.

The plants were slightly powdered with carborundum through double cheesecloth. A sponge was dipped into the inoculi and twice wiped out over the total surface of both cotyledons. Although the virus was stable, the infection time should be shorter than 1 hour.
Evaluation The first two leafs of the cucumber plants will not show symptoms (in susceptible plants as well in resistant plants). From the third to the fourth leaf stage, symptoms will be easy to score susceptible or resistant.

Example 2

Identification of AFLP Markers Identifying a Tobamovirus Resistance QTL

Introduction

In this example, a Qualitative Trait Locus (QTL) was identified in resistant cucumber plants (*Cucumis sativus* L.) by use of a Bulk QTL Analysis (BQA), performed by Keygene N. V. (Wageningen, The Netherlands). A population of 98 individuals for marker development for tobamovirus resistance was selected. A total of 96 AFLP primer combinations were screened on two pools containing individuals showing 'extreme phenotypes' for tobamovirus resistance. Subsequently, five candidate markers were verified on 12 resistant and 12 susceptible individuals.
Marker Identification and Verification Leaf material of 130 plants was obtained: a Cuc1879-01× OK561 population of 98 individuals to provide the population to be tested, 30 inbred lines of the donor parent Cuc1879-01 and the parental lines of the population. DNA was isolated and EcoRI/MseI templates were generated. A test fingerprint of the 130 plants was generated using primer combination E14/M59.
BSA and Verification on Individuals The BQA was performed by screening a total of 96 primer combinations on a pool containing ten 'extreme resistant' individuals and a pool containing ten 'extreme susceptible' individuals. This screening resulted in the identification of the following candidate markers:

E14/M58-F-169-P2

E22/M48-F-248/246 (bi-allelic)

These markers were subsequently verified on 24 individuals (12 resistant individuals and 12 susceptible individuals). Based on this verification the candidate markers identified proved to be linked to tobamovirus resistance.
Verification of Candidate Markers on the Population After screening the 96 primer combinations and subsequent validation of the markers, one putative QTL could be identified. In order to determine whether the QTL identified is indeed a separate QTL a linkage analysis was executed.

Markers (E14/M58-F-169-P2 and the biallelic marker E22/M48-F-248/246) were screened on 46 additional individuals from the population of 98 individuals.

A marker dataset was generated and merged with the marker dataset of the verification on the 24 individuals. Based upon this analysis, it could be concluded that the four markers are indeed linked to one QTL.
Marker Analysis Using WinQTLCartographer In order to determine the correlation between the phenotype and genotype, the marker dataset was analyzed using the software package WinQTLCartographer. For Single Marker Analysis (SMA) a LOD value of 12 was calculated. For Interval Mapping (IM) the 95% reliable threshold was calculated by performing 1000 permutations on the phenotype data and was determined as LOD 0.9. The LOD value and percentage explained variances were calculated for this QTL (LOD: 9; Exp. Var.: 49.5).

CONCLUSION

In order to identify a QTL for tobamovirus resistance, a BQA was performed. A total of 96 primer combinations were screened on a bulk of ten 'extreme resistant' individuals and a bulk of ten 'extreme susceptible' individuals. Candidate markers, of which one was bi-allelic, were verified on 12 'extreme resistant' and 12 'extreme susceptible' individuals and on 48 other individuals of the population. A QTL region was identified by using a BQA approach. This QTL explains ~50% of the variance. Based on the TestPC (~five markers) no heterogenity was identified in the 30 inbred lines of the resistant donor parent Cuc1879-01.

Example 3

Molecular Marker Assisted Identification of Tobamovirus Resistant Cucumber Plants (Cucumis sativus L.)

Molecular Analysis

From both susceptible, i.e., showing one or more of the symptoms of a viral infection as described above, and resistant individual cucumber plants (Cucumis sativus L.) genomic material was isolated using standard protocols.

Subsequently, this genomic material was digested using the appropriate restriction enzymes (EcoRI/MseI) and, after ligation of the adapters, subjected to AFLP nucleic acid amplification using primer pair SEQ ID No: 1 5'-GAC TGC GTA CCA ATT CGT-3' and SEQ ID No: 2 5'-GAT GAG TCC TGA GTA ACA C-3' or primer pair SEQ ID No: 3 5'-GAC TGC GTA CCA ATT CAT-3' and SEQ ID No: 4 5'-GAT GAG TCC TGA GTA ACG T-3'.

The resulting amplification products were resolved by gelelecrophoresis for size determination. The presence of AFLP markers in the genomes of the individual cucumber plants (Cucumis sativus L.) were detected as absent (−) or as present (+).

Specifically, when AFLP Marker E14/M58-F-169 (not encompassed by the present invention, SEQ ID NOs: 3 and 4) was present, a band of approximately 169 by was observed; when AFLP Marker E22/M48-F-248 (not encompassed by the present invention, primers SEQ ID No: 3 and 4) was present, a band of approximately 248 by was observed. AFLP marker E14/M48-F-246 (encompassed by the present invention, primers SEQ ID No: 3 and 4) with an estimated size of approximately 246 by genetically correlated with the resistant phenotype The results are summarized in Table 1 below.

TABLE 1

Correlation between AFLP markers E14/M58-F-169; E22/M48-F-246; and E22/M48-F-248 and a tobamovirus resistant phenotype

| Individual cucumber plants (Cucumis sativus L.) | Phenotype | E14/M58-F-169 | E22/M48-F-246 | E22/M48-F-248 |
|---|---|---|---|---|
| TLCG04_4816_10 | susceptible | + | − | + |
| TLCG04_4816_18 | susceptible | + | − | + |
| TLCG04_4816_133 | susceptible | + | − | + |
| TLCG04_4816_23 | susceptible | + | − | + |
| TLCG04_4816_24 | susceptible | + | − | + |
| TLCG04_4816_31 | susceptible | + | − | + |
| TLCG04_4816_43 | susceptible | + | − | + |
| TLCG04_4816_56 | susceptible | + | − | + |
| TLCG04_4816_57 | susceptible | + | − | + |
| TLCG04_4816_61 | susceptible | + | − | + |
| TLCG04_4816_64 | susceptible | + | − | + |
| TLCG04_4816_66 | susceptible | + | − | + |
| T33169_9 | resistant | − | + | − |
| T33168_2 | resistant | − | + | − |
| T33168_4 | resistant | − | + | − |
| T33168_5 | resistant | − | + | − |
| T33168_6 | resistant | − | + | − |
| T33168_7 | resistant | − | + | − |
| T33168_8 | resistant | − | + | − |
| T33168_9 | resistant | − | + | − |
| T33169_2 | resistant | − | + | − |
| T33169_3 | resistant | − | + | − |
| T33169_5 | resistant | − | + | − |
| T33169_6 | resistant | − | + | − |

Table 1 clearly shows that resistance against CGMMV and CFMMV is in all cucumber plants (Cucumis sativus L.) tested genetically linked with the presence of molecular AFLP marker E22/M48-F-246. Thus, the detecting this marker indicates the presence of a tobamovirus resistance genetic locus or QTL.

LITERATURE

Ainworth, G. C. 1935. *Mosaic disease of cucumber.* Ann Appl. Biol. 22:55-67.

Antignus, Y. 2001. *Biological and Molecular Characterization of a New Cucurbit-Infecting Tobamovirus.* Phytopathology Vol. 91, No 6, 2001 565-571.

Rashmi, C. M. 2005. *Natural occurrence of Cucumber green mottle mosaic virus on gherkins (Cucumis anguria L.)* Evironment and Ecology. 2005; 23S(special 4):781-784.

Varveri, V. 2002. *Characterization and detection of Cucumber Green Mottle Mosaic Virus in Greece.*

Dorst, H. J. M. van. 1988. *Surface water as a source in the spread of cucumber green mottle mosaic virus.* Netherlands Journal of Agricultural Science. 1988; 36(3):291-299.

Hsiao, C. H. 1993. *Screening and breeding for resistance to viruses in cucurbits.* Plant Pathology Bulletin. 1993; 2(4): 241-248.

Fletcher. 1962; Plant Pathology 18; 16.

Hollings, M. 1975. *Cucumber green mottle mosaic virus.* Description of Plant viruses No. 154.

Celix, A. 1996. *First report of cucumber green mottle mosaic tobamovirus infecting greenhouse grown cucumber in Spain.* Plant Disease. 1996; 80(11):1303.

Kim SangMin 2003. *Destruction of green mottle mosaic virus by heat treatment and rapid detection of virus inactivation by TR-PCR.* Molecules and Cells. 2003; 16(3):338-342.

Kooistra E. *Significance of the non-appearance of visible disease symptoms in cucumber (Cucumis sativus L.) after infection with Cucumis virus 2.* Euphytica 17 (1968): 136-140.

Vos, P., Rogers, R, Bleeker, M., et al. 1995. *AFLP: a new technique for DNA fingerprinting.* Nucleic Acids Research 23(21): 4407-4414.

Zabeau, M and P. Vos. 1993. *Selective restriction fragment amplification: a general method for DNA fingerprinting.* European Patent Office, publication 0 534 858 A1, bulletin 93/13.

The invention claimed is:

1. Method for providing a tobamovirus resistant cucumber plant (*Cucumis sativus* L.) comprising:

(a) identifying a tobamovirus resistance genetic locus in a first cucumber plant (*Cucumis sativus* L.);

(b) transferring the identified tobamovirus resistance genetic locus into a second cucumber plant (*Cucumis sativus* L.) thereby conferring tobamovirus resistance to said second cucumber plant;

wherein said identifying a tobamovirus resistance genetic locus comprises using a molecular marker for identifying a tobamovirus resistance genetic locus in the genome of said first cucumber plant, said genetic locus is identified by a nucleic acid amplification fragment of 245-247 bp using molecular amplified fragment length polymorphism (AFLP) primers SEQ ID NO: 1 and SEQ ID NO: 2 in an AFLP assay, and wherein said tobamovirus resistance comprises cucumber green mottle mosaic virus (CGMMV) resistance and cucumber fruit mottle mosaic virus (CFMMV) resistance.

2. Method according to claim 1, wherein the nucleic acid amplification fragment is 246 bp.

3. A cucumber plant (*Cucumis sativus* L.) obtained by the method according to claim 1, comprising the genotype of a tobamovirus susceptible cucumber plant (*Cucumis sativus* L.) variety supplemented with a tobamovirus resistance genetic locus, wherein said tobamovirus resistance comprises cucumber green mottle mosaic virus (CGMMV) resistance and cucumber fruit mottle mosaic virus (CFMMV) resistance.

4. Plant according to claim 3, wherein the nucleic acid amplification fragment is 246 bp.

5. Seeds, plant parts, or fruits of a plant according to claim 3; wherein said seeds, plant parts, or fruits of a plant comprise a tobamovirus resistance genetic locus.

* * * * *